United States Patent
Lee

(10) Patent No.: US 8,568,988 B2
(45) Date of Patent: Oct. 29, 2013

(54) USE OF CFH OR APOH AS A BIOCHEMICAL DIAGNOSTIC MARKER FOR COMPLETE REMISSION IN ACUTE MYELOID LEUKEMIA

(75) Inventor: Seung Won Lee, Gwangju (KR)

(73) Assignee: Industry Foundation of Chonnam National University, Gwangju (KR)

( * ) Notice: Subject to any disclaimer, the term of this patent is extended or adjusted under 35 U.S.C. 154(b) by 388 days.

(21) Appl. No.: 12/874,612

(22) Filed: Sep. 2, 2010

(65) Prior Publication Data

US 2011/0053190 A1    Mar. 3, 2011

Related U.S. Application Data

(63) Continuation-in-part of application No. PCT/KR2010/002273, filed on Apr. 13, 2010.

(30) Foreign Application Priority Data

Apr. 20, 2009    (KR) .................. 10-2009-0034324

(51) Int. Cl.
  *G01N 33/53*    (2006.01)
  *G01N 33/567*    (2006.01)
  *G01N 33/574*    (2006.01)

(52) U.S. Cl.
  USPC .................... 435/7.1; 435/7.21; 435/7.23

(58) Field of Classification Search
  None
  See application file for complete search history.

(56) References Cited

PUBLICATIONS

Boyd, N. F. teaches (The Basic Science of Oncology, Tannock and Hill eds. 1992, Ch. 21, p. 379-394).*
Matsuda et al. (Amer. J. Hematology 1993 42(2):234-235).*
Stites et al. (Medical Immunology, 9th Ed, Appleton and Lange, 1997, pp. 250-251).*
Cheson et al., "Revised Recommendations of the International Working Group for Diagnosis, Standardization of Response Criteria, Treatment Outcomes, and Reporting Standards for Therapeutic Trials in Acute Myeloid Leukemia," J. Clin. Oncol. 21:4642-4649, 2003.
De Greef et al., "Criteria for Defining a Complete Remission in Acute Myeloid Leukaemia Revisited. An Analysis of Patients Treated in HOVON-SAKK Co-Operative Group Studies," Brit. J. Haematol. 128:184-191, 2004.
Ishihama et al., "Exponentially Modified Protein Abundance Index (emPAI) for Estimation of Absolute Protein Amount in Proteomics by the Number of Sequenced Peptides Per Protein," Mol. Cell Proteomics 4:1265-1272, 2005.
Wu et al., "Targeted Proteomics of Low-Level Proteins in Human Plasma by LC/MS$^n$: Using Human Growth Hormone as a Model System," J. Proteome Res. 1:459-465, 2002.

* cited by examiner

*Primary Examiner* — Peter J Reddig
(74) *Attorney, Agent, or Firm* — Clark & Elbing LLP

(57) ABSTRACT

The present invention relates to a diagnostic method for acute myeloid leukemia, in particular, a method for using CFH or ApoH in patient sera as biochemical diagnostic markers to determine complete remission in acute myeloid leukemia. In accordance with this invention, CFH and ApoH are identified as a novel biochemical marker for understanding the biological mechanism and responsiveness to disease in AML patients after induction chemotherapy, and can be used as a biochemical marker for evaluating the prognosis of disease in patients after induction chemotherapy.

7 Claims, 9 Drawing Sheets

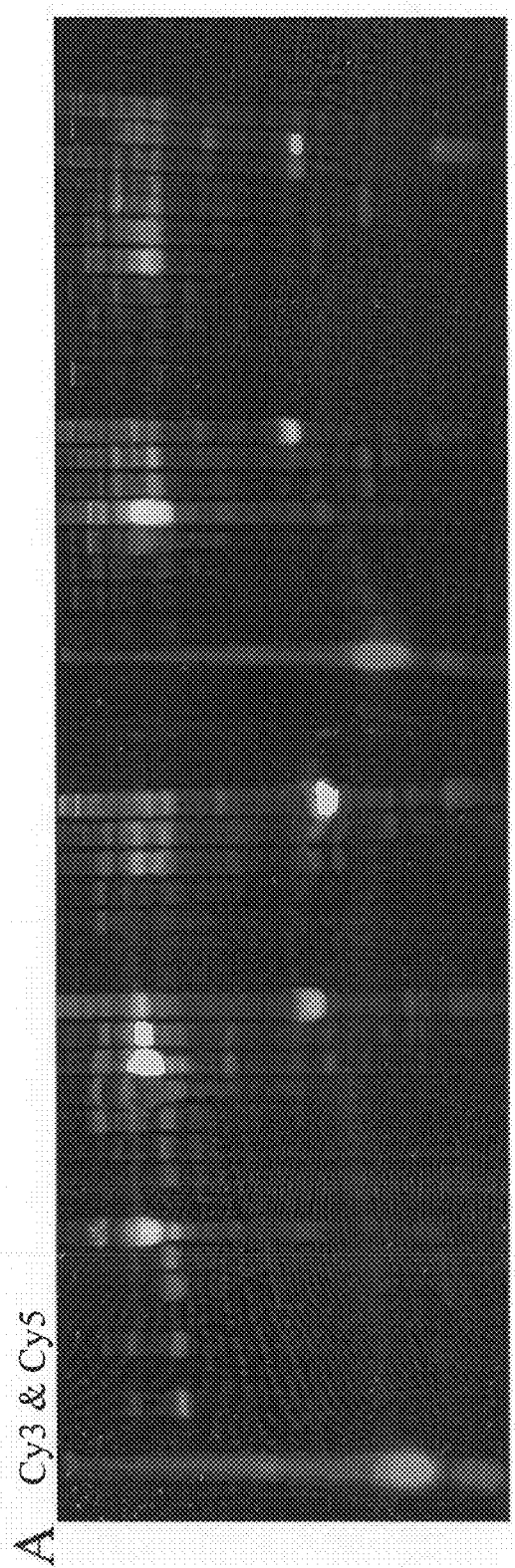

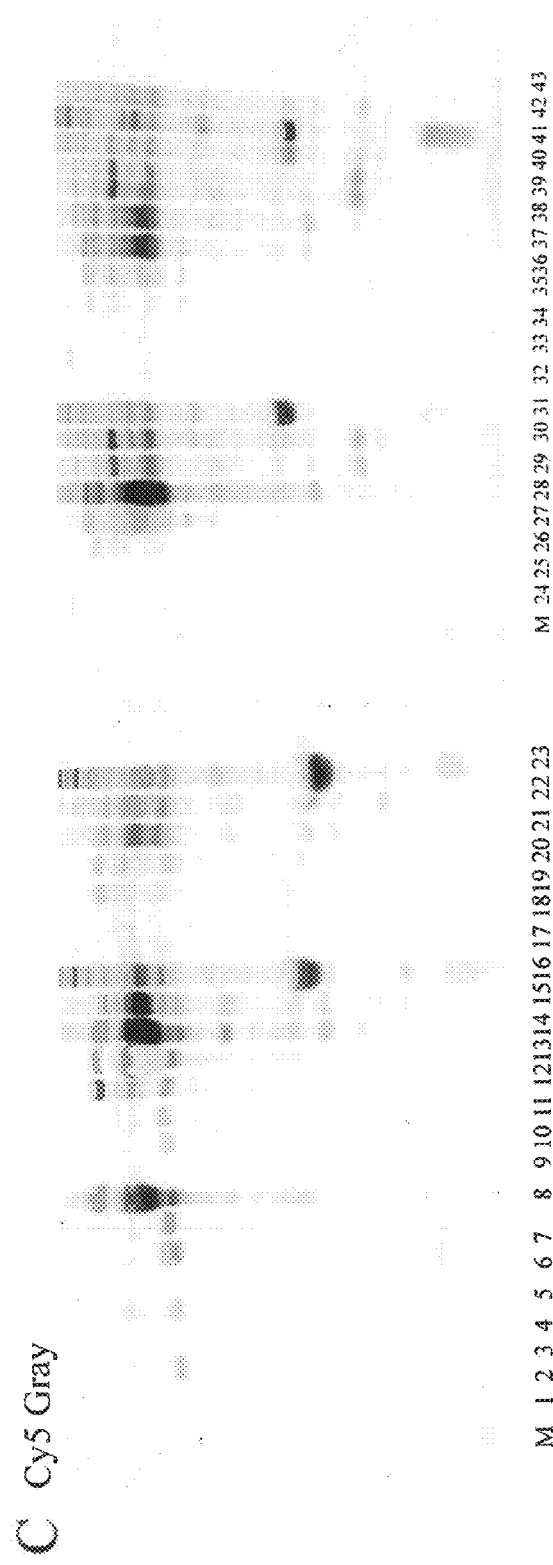

CFH

APOH

CFH

APOH

USE OF CFH OR APOH AS A BIOCHEMICAL DIAGNOSTIC MARKER FOR COMPLETE REMISSION IN ACUTE MYELOID LEUKEMIA

RELATED APPLICATIONS

This is a continuation-in-part of PCT/KR2010/002273, filed on Apr. 13, 2010, which claims priority from Korean Patent Appln. No. 2009-0034324, filed on Apr. 20, 2009, in the Korean Intellectual Property Office, the disclosure of which is incorporated herein by reference.

BACKGROUND OF THE INVENTION

1. Field of the Invention

The present invention relates to a diagnostic method for acute myeloid leukemia, in particular, a method for using CFH or ApoH in patient sera as biochemical diagnostic markers to determine complete remission in acute myeloid leukemia.

2. Description of the Related Art

Acute myeloid leukemia (AML) is a disease characterized by infiltration of neoplastic myeloid cells of the hematopoietic system into blood and bone marrow that leads to rapid devastation in patients when left untreated. One of the well-known approaches for treating AML patients is the risk-adapted therapy. To achieve this goal, it should be first determined whether the patient is free of leukemic cells after chemotherapy or not (i.e., achievability of complete remission).

The curability of AML is influenced by many pretreatment factors, such as patient's age, chromosomal abnormalities, hematological disorders, leukocyte count and leukemic cell characteristics. In addition to these variables, several treatment factors including complete remission achievement are correlated with the prognosis of AML, such as achieving complete remission.

Complete remission is the primary endpoint following induction chemotherapy in AML patients. According to the International Working Group (IWG) recommendations for diagnosis and standardization criteria in AML, which were published in 1990 and recently revised, a designation of CR (morphologic complete remission) requires that the patient achieves a morphologically leukemia-free state (<5% blasts in aspirate sample containing marrow spicules and ≥200 nucleated cells) and has absolute neutrophil and platelet counts of >1,000 µl and >100,000 µl, respectively. Blasts with Auer rods or the persistence of extramedullary disease should not be present.

All of the IWG criteria are related to increased overall survival (OS) and decreased relapse risk (RR). CR may be considered as a state in which the hematopoietic system of an AML patient responds favorably to further treatment.

In contrast, the state designed as non-remission (NR), in which AML patients do not achieve CR, is associated with a less-favorable hematopoietic responses. The NR category of AML patients after chemotherapy may include cases that do not fulfill all of the CR requirements, such as (i) patients who are not in the morphologic leukemia-free state (≥5% blasts in BM aspirate) but whose blood counts are in the recovery state (neutrophil and platelet counts >1,000/µl and >100,000/µl, respectively), (ii) those in the morphologic leukemia-free state (<5% blasts in BM aspirate) but not in the blood count recovery state (neutrophil and platelet counts 1,000/µl and 100,000/µl, respectively), and (iii) those neither in the morphologically leukemia-free state (≥5% blasts in BM aspirate) nor in the blood count recovery state (neutrophil and platelet counts ≤1,000/µl and ≤100,000/µl, respectively).

However, BM blasts including leukemic blasts frequently lost their classical morphology after chemotherapy resulting in difficulty in the differential count of BM cells. Also normal blood cells can lose their classical morphology after chemotherapy. Therefore, it is often difficult to use blood counts after cancer chemotherapy. In these cases, having a serum CR marker which can replace differential count of BM cells or normal blood counts, it would be an important diagnostic method which can be a supplementary thing or replace the conventional method.

Accordingly, the investigation of new biochemical markers was strongly required for analyzing responsiveness to chemotherapies in sera from AML patients.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have conducted intensive research to identify biochemical markers that could determine whether AML patients achieved or failed complete remission after chemotherapy.

Accordingly, it is an object of this invention to identify CFH or ApoH in AML patient sera as new biochemical markers to understand the biological mechanism of the human body in response to AML treatment, and to provide a method to apply CFH or ApoH as diagnostic biochemical markers to determine the recovery state of AML patients.

It is another object of this invention is to provide much more accurate methods for determining the recovery state from AML, by using CFH or ApoH as biochemical markers in sera from AML patients, because CFH or ApoH level in sera reflects CR or NR of AML patients after chemotherapy, in other words, good or bad prognosis of AML after chemotherapy.

Other objects and advantages of the present invention will become apparent from the following detailed description together with the appended claims and drawings.

BRIEF DESCRIPTION OF THE DRAWINGS

FIGS. 4A-4D shows PAGE separation images of Cy dye-labeled pooled PreCR and CR proteins that were previously fractionated by CF and RP chromatography. Panel A: Merged image of Cy3-labeled (green; PreCR) and Cy5-labeled (red; CR) serum samples; Panel B: Gray image of Cy3-labeled samples, as in FIG. 2; Panel C: Gray image of Cy5-labeled samples, as in FIG. 2; Panel D: Coomassie blue-stained image of the identical gel. Bands A, B, C, D, and E are stained successfully with a commercial staining solution (Simply Blue SafeStain™) among the bands showing signals with Cy3/Cy5 or Cy5/Cy3 dye ratios of ≥2.0, which were subsequently excised for the identification of the corresponding proteins.

DETAILED DESCRIPTION OF THIS INVENTION

Figure 1:
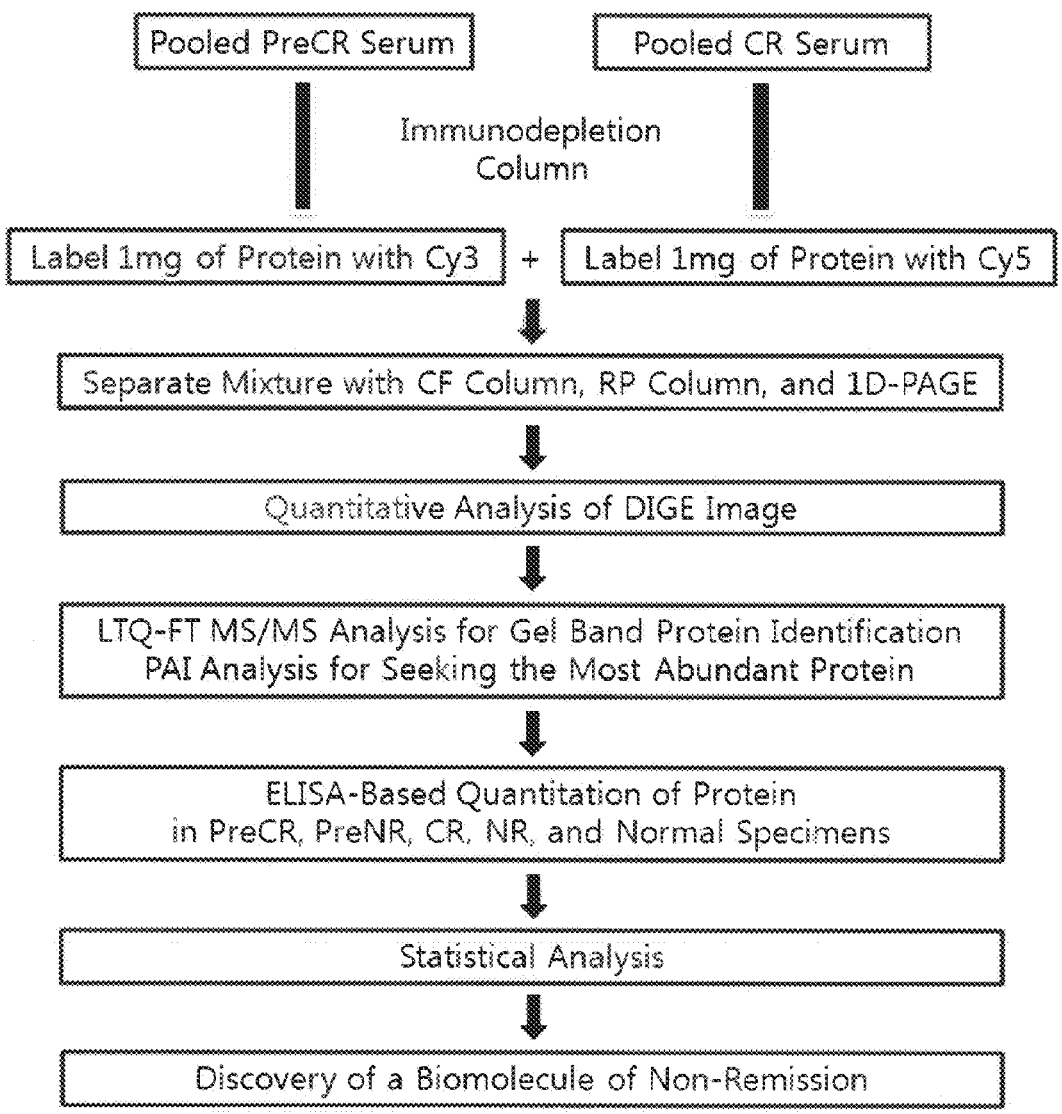
FIG. 1 represents a workflow chart of the experimental procedures used to identify CFH or ApoH, the biomarkers of CR vs. non-CR (NR) in AML patients as described in the Method of this invention.

To achieve the above-mentioned objects of this invention, the present invention provides a method for detecting a biochemical marker indicating complete remission in a patient with acute myeloid leukemia (AML) after chemotherapy by measuring the level of CFH (complement factor H) or ApoH (apolipoprotein H) in a sample from AML patient, whereby information for determining complete remission or non-remission in AML is provided.

In an aspect of the present invention, there is provided a method for determining complete remission or non-remission in a patient with acute myeloid leukemia (AML) after chemotherapy, which comprises measuring the level of CFH (complement factor H) or ApoH (apolipoprotein H) in a biological sample from the AML patient, wherein an increased level of CFH or ApoH compared to a normal human indicates that the patient is in a non-remission in AML, and wherein a similar level of CFH or ApoH to the normal human indicates that the patient achieves complete remission in AML.

The present invention may use various biological samples from AML patients after chemotherapy. Preferably, the biological sample is a body fluid sample drawn from human including blood, serum, plasma, lymph, milk, urine, faeces, ocular fluid, saliva, semen, spinal cord fluid. More preferably, the biological sample is blood, serum or plasma, most preferably serum.

The biological sample is drawn from human patients, preferably human patients treated with various drugs for AML, e.g., idarubicin, cytosine arabinoside (ara-C), BH-AC, ATRA and Gleevec.

Where the level CFH or ApoH in human patients is analyzed to be similar to that in a normal (or healthy) human, the patient can be determined to achieve complete remission in AML.

The phrase "similar level of CFH or ApoH to a normal human" means levels of CFH or ApoH similar to what would normally be observed in a comparable biological sample from control or normal subjects. In the present application, "control levels" (i.e. normal levels) refer to a range of CFH or ApoH levels that would be normally expected to be observed in human that does not have a hematological disorder, in particular, AML.

Preferably, the similar level of CFH or ApoH to a normal human means a range of CFH or ApoH levels that would be normally expected to be observed in human that does not have AML.

More preferably, the similar level of CFH or ApoH to the normal human indicating complete remission is between +50 μg/ml and −50 μg/ml of a level of CFH or ApoH in the normal human (normal levels of CFH or ApoH±50 μg/ml). For instance, the similar level of CFH or ApoH to the normal human is preferably 170±100 μg/ml, more preferably, 170±90 μg/ml, still more preferably 170±80 μg/ml.

According to a preferred embodiment, the patient with AML is determined to achieve complete remission in AML when the level of CFH or ApoH is measured to be 130-250 μg/ml. More preferably, the patient with AML is determined to achieve complete remission in AML when the level of CFH is measured to be 176.82±28.17 μg/ml. More preferably, the patient with AML is determined to achieve complete remission in AML when the level of ApoH is measured to be 181.55±39.81 μg/ml.

Where the level CFH or ApoH in human patients is analyzed to be higher than that in a normal (or healthy) human, the patient can be determined to be in a non-remission in AML The term "higher levels" as used herein refers to levels of CFH or ApoH, that are higher than what would normally be observed in a comparable biological sample from control or normal subjects. In some embodiments of the invention "control levels" (i.e. normal levels) refer to a range of CFH or ApoH levels that would be normally be expected to be observed in human that does not have a hematological disorder, in particular, AML. and "higher levels" refer to CFH or ApoH levels that are above the range of control levels. The ranges accepted as "higher levels" are dependant on a number of factors. For example, one laboratory may routinely determine absolute levels of CFH or ApoH in a sample that are different than the absolute levels obtained for the same sample by another laboratory. Also, different assay methods may achieve different value ranges. Value ranges may also differ in various samples or by different treatments of the samples. One of ordinary skill in the art is capable of considering the relevant factors and establishing appropriate reference ranges for "control values" and "higher values" of the present invention. For example, a series of samples from control subjects and subjects diagnosed with AML can be used to establish ranges that are "normal" or "control" levels and ranges that are "higher" than the control range.

According to a preferred embodiment, the patient with AML is determined to be in non-remission in AML when the level of CFH or ApoH is measured to be 500-700 μg/ml. More preferably, the patient with AML is determined to be in non-remission in AML when the level of CFH is measured to be 617.7±43.19 μg/ml. More preferably, the patient with AML is determined to be in non-remission in AML when the level of ApoH is measured to be 606.6±48.79 μg/ml.

The levels of CFH or ApoH may be measured by a variety of genetic or protein assays known in the art. For example, the levels of biomarkers may be evaluated by mass spectrometry, immunoassay, immuno-mass spectrometry and suspension bead array. Preferably, the levels of CFH or ApoH are analyzed by protein assays. More preferably, the measurement of the level of CFH or ApoH is performed by immunoassay.

The present method may be performed pursuant to the immunoassay procedure known to one skilled in the art. The immunoassay format includes, but not limited to, radioimmunoassay, radioimmuno-precipitation, enzyme-linked immunosorbent assay (ELISA), capture-ELISA, dot blot assay, Western blot assay, inhibition or competition assay, sandwich assay, flow cytometry and immunofluorescence staining. The immunoassay procedures can be found in *Enzyme Immunoassay*, E. T. Maggio, ed., CRC Press, Boca Raton, Fla., 1980;

Gaastra, W., Enzyme-linked immunosorbent assay (ELISA), in *Methods in Molecular Biology*, Vol. 1, Walker, J. M. ed., Humana Press, NJ, 1984; and Ed Harlow and David Lane, *Using Antibodies*, A Laboratory Manual, Cold Spring Harbor Laboratory Press, 1999.

For example, according to the radioimmunoassay method, the radioisotope (e.g., $P^{32}$ and $S^{35}$) labeled antibody may be used to analyze CFH or ApoH in a sample.

According to the ELISA method, the specific example of the present method may comprise the steps of: (i) coating a surface of a solid substrate with a biosample to be analyzed; (ii) incubating the biosample with monoclonal antibody to CFH or ApoH as a primary antibody; (iii) incubating the resultant of step (ii) with a secondary antibody conjugated to an enzyme catalyzing colorimetric, fluorometric, luminescence or infra-red reactions; and (iv) measuring the activity of the enzyme.

The solid substrate coated may include hydrocarbon polymers such as polystyrene and polypropylene, glass, metals, and gels. The solid substrate may be in the form of a dipstick, a microliter plate, a particle (e.g., bead), an affinity column and an immunoblot membrane (eg, polyvinylidene fluoride membrane) (see U.S. Pat. Nos. 5,143,825, 5,374,530, 4,908, 305 and 5,498,551). Most preferably, the solid substrate is a microliter plate.

The enzyme catalyzing colorimetric, fluorometric, luminescence or infra-red reactions includes, but not limited to, alkaline phosphatase, β-galactosidase, Cytochrome $P_{450}$, and horseradish peroxidase. Where using alkaline phosphatase, bromochloroindolylphosphate (BCIP), nitro blue tetrazolium (NBT) and ECF (enhanced chemifluorescence) may be used as a substrate; in the case of using horseradish peroxidase, chloronaphtol, aminoethylcarbazol, diaminobenzidine, D-luciferin, ludgenin(bis-N-methylacridinium nitrate), resorufin benzyl ether, luminol, Amplex Red reagent (10-acetyl-3,7-dihydroxyphenoxazine, Pierce), TMB (3,3,5,5-tetramethylbenzidine) and ABTS (2,2-Azine-di[3-ethylbenzthiazoline sulfonate]) may be used as a substrate.

Alternatively, the levels of CFH or ApoH may be measured by using mass spectrometry-based MRM (multiple reaction monitoring). This technique applies the MS/MS approach to, for quantification of the surrogate peptide (protein of interest) relative to the externally mixed standard peptide, tryptic digests of the protein sample, followed by selected ion partitioning and sampling using MS to objectify and discretize the analyte by detecting the exact m/z ion of the tryptic fragment that represents the protein (Andersen et al, *Molecular and Cellular Proteomics*, 5.4:573-588(2006); Whiteaker et al, *J. Proteome Res.* 6.10:3962-75(2007)). In addition, the levels of CFH or ApoH may be evaluated by modifications of MRM such as SISCAPA (Stable Isotope Standards and Capture by Anti-Peptide Antibodies; Anderson, N. L. et al., *J Proteome Res.* 3:235-244(2004)).

In this invention, to investigate a biochemical marker representing the response to the disease in AML patients after chemotherapy, serum was pooled from patients who have achieved CR and applied to multidimensional liquid chromatography-differential gel electrophoresis (MDLC-DIGE) for protein profiling.

DIGE data obtained from samples previously separated by MDLC were normalized, estimated with exponentially modified protein abundance index (emPAI), and the protein was identified using LTQ-FT MS/MS technique. Two differentially expressed proteins complement factor H (CFH) and apolipoprotein H (ApoH) were identified from the analysis of two pooled samples, PreCR (a pooling of sera from AML patients prior to chemotherapy) and CR (a pooling of sera from the same patients after achieving CR).

ELISA-based protein quantification of CFH and ApoH were performed using the sera from AML patients in various states, including PreCR and patients who achieved remission after chemotherapy (CR), as well as for samples taken prior to (PreNR) and from patients who failed to achieve CR after chemotherapy (non-remission, NR) and from healthy control subjects (Normal).

Comparison of the CFH and ApoH levels among combinations of the two groups (PreCR vs. CR, PreNR vs. NR, PreNR vs. PreCR, NR vs. CR, and CR vs. Normal) revealed statistically significant differences between the recovered (CR and Normal) and non-recovered groups (PreCR, PreNR, and NR).

The present invention demonstrated that CFH and ApoH are valuable markers for distinguishing CR and NR states in AML patients after remission-induction chemotherapy.

The present invention has the following advantages:

First, according to this invention, CFH or ApoH are identified as a novel biochemical marker for understanding the biological mechanism and responsiveness to disease in AML patients after induction chemotherapy, can be used as a biochemical marker for complete remission achievement in an AML patient after induction chemotherapy, thus replacing or complementing conventional diagnostic methods such as differential counting of BM blasts or normal blood cells to determine CR or NR state in AML patients.

In addition, according to this invention, by detecting the concentration of CFH and ApoH in patient sera provides more accurate diagnostic methods for evaluating the prognosis of AML, because CFH and ApoH concentration in serum indicates CR or NR of AMP patients, which reflects either good or bad prognosis of the disease in AML patients after chemotherapy.

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods

1. Patients, Specimens, and Post-Chemotherapy Response Criteria

The serum specimens used in the study were obtained from Genome Research Center for Hematopoietic Diseases (GRCHD) at Chonnam National University Hospital, which is a tertiary care center. Clinical information was obtained by chart review, and all diagnoses were performed based on histological data collected from BM samples. At the time of BM sample collection, the subjects were provided informed consent to allow post-examination specimens to be used for further research-only purposes, and this study was reviewed and approved by the Institutional Review Board. Serum samples were immediately placed on ice for transport to the laboratory, where they were centrifuged, aliquoted, and frozen at −80° C. until use.

The patients in the present study were divided into two groups, CR and NR, according to their responses to idarubicin/BH-AC and ATRA (only for M3 AML) remission-induction chemotherapy (Table 1). The post-chemotherapy BM aspirate (serum) was collected from the AML patients 1 month after chemotherapy. Of the archived specimens, 66 were from 33 patients in the CR state, and 40 were from 20 patients in the NR state. Two samples were taken from each patient; the first sample were taken at the time of the diagnosis of AML (PreCR and PreNR samples), and the second sample were taken immediately after one month of remission-induction chemotherapy (CR and NR samples). Twenty-five samples taken from healthy subjects were included in this study as controls (Normal samples).

2. Cy Dye Labeling of Pooled PreCR and CR Serum Proteins

Aliquoted 30 μl of PreCR and CR serum samples from 33 CR patients were combined to generate about 1 ml of pooled PreCR serum and about 1 ml of pooled CR serum, respectively. Highly abundant proteins, such as albumin and IgG, were removed from each pooled serum sample using a multiple affinity removal system (MARS; Agilent Technologies, San Diego, Calif.) according to the manufacturer's protocol. The flow-through fractions (PreCR and CR) were concentrated in a 5,000 molecular weight cut off concentrator. The protein contents of the concentrated samples were quantified, 1 mg of protein was taken, the volume was adjusted to 1 ml in lysis buffer (30 mM Tris [pH 8.5], 8 M urea, 4% CHAPS), and then placed on ice.

The Cy3 and Cy5 dyes were used to label the PreCR and CR pooled samples, respectively. Briefly, the Cy dyes were each resuspended in N,N-dimethylformamide at a concentration of 0.4 mM (400 pmol/μl), and then allowed to react with the serum proteins at a ratio of 400 pmol: 50 μg for Cy dye: protein (i.e., 20 μl of Cy dye per 1 mg of protein). Cy labeling of the —$NH_2$ groups of the lysine residues was performed on ice in the dark for 30 min. The reaction was quenched by the addition of 20 μl of 10 mM L-lysine for 10 min. The Cy3- and Cy5-labeled serum proteins were mixed, wrapped in aluminum foil, and frozen at −80° C. until use.

3. Fractionation and Separation of Cy Dye-Labeled Serum Protein Mixtures

A flowchart for the Cy dye-labeled protein mixture separation and subsequent evaluation is shown in FIG. 1. Mixed paired serum protein samples were first separated by chromatofocusing (CF) chromatography (Tricom High Performance Columns, Mono P 5/200GL System; Amersham Biosciences, Wikströms, Sweden) using a ProteomeLab HPLC system (Beckman Coulter, Fullerton, Calif.). The UV detector wavelength was set at 280 nm, and protein separation was performed over a pH range of 9.0-4.0 with a pH interval of 0.2. The CF column was equilibrated in Buffer A (0.075 M Tris [pH 9.3]) for 20-30 min at a flow rate of 1 ml/min. Aliquots of 2 ml of the mixed serum proteins were injected into the column. Buffer A was allowed to pass through the column for 10 min at a flow rate of 0.5 mi/min, and bound proteins were eluted from the column in Buffer B (Polybuffer 74, pH 4.0; Amersham Biosciences) for 40 min at 0.5 ml/min, after which the column was washed with Buffer C (1 M NaCl) for 30 min at 0.5 ml/min and with Buffer D (dd$H_2$O) for 30 min at 0.5 ml/min. In total, eight fractions were collected into separate vials and stored at 4° C. until use.

Each of the eight fractions was further separated by reversed-phase (RP) chromatography (SOURCE 15RPC ST 4.6/100; Amersham Biosciences) in the second dimension, using the ProteomeLab HPLC system (Beckman Coulter). The UV detector wavelength was set at 214 nm, and the eluted protein fractions were collected at 30-sec intervals. The RP column was equilibrated in Buffer A (100% $H_2O$, 0.1% TFA) for 30-60 minutes at a flow rate of 1 ml/min. The eight fractions were each concentrated to about 150 μl and the volumes were adjusted to 700 μl in Buffer A. Then, 500 μl of each sample were injected into the column using an autosampler. Buffer A was allowed to pass through the column for 1 min at a flow rate of 0.75 ml/min, and elution was performed with Buffer B (100% ACN, 0.08% TFA) in a gradient from 0% to 100% over 44 min at a flow rate of 0.75 mi/min. The gradient (Buffer B) was then returned to 0% over 1 min. The column was re-equilibrated in Buffer A for 20 min before the next run. In total, 17-20 fractions from chromatography in the second dimension were collected from each first-dimension fraction, and the total number of second-dimension fractions was 144.

The amount of protein in each RP (or second-dimension) fraction from the eight CF (or first-dimension) fractions was calculated on the basis of the chromatographic area measurement. The neighboring fraction samples were then pooled so that the total chromatographic amount of protein was similar across the new pooled fractions. There were 43 fractions. Each second-dimension fraction was further separated by SDS-PAGE. The fractions were lyophilized and dissolved in 20 μl of sample buffer (120 mM Tris-HCl [pH 6.6], 10% SDS, 20% glycerol, 3% DTT, 0.03 M bromophenol blue). After boiling for 5 min, the protein samples were loaded onto 12% polyacrylamide gels measuring 18×16 cm between glass plates (low fluorescence; Amersham Biosciences). Proteins were electrophoresed at 40 mA in the stacking gel and then at 80 mA in the separation gel.

4. Cy Dye-Labeled Protein Visualization and Image Analysis

Gels were scanned directly using a 9200 Typhoon Scanner (GE Healthcare, Chalfont St. Giles, UK). Cy3- and Cy5-labeled protein bands were scanned with the Typhoon Scanner Control software, with the settings of: Cy3 channel at 532 nm, PMT (photomultiplier tube) at 510 V; Cy5 channel at 633 nm, PMT at 490 V. The scanned images were analyzed with the ImageQuant TL software (GE Healthcare).

First, the bands for Cy dye-labeled proteins were detected, and the fluorescence intensities were measured as Area×Density. The detected bands were aligned, and the matched and unmatched volumes were all indicated. For all the matched volumes, the Cy3/Cy5 ratio was calculated and normalization was performed from the histogram of Cy3/Cy5 ratio distribution (central 90%). After this normalization process, the thresholds for assigning differential expression between the pooled PreCR and CR samples were set at a minimum 2.0-fold change.

Before excision of bands for protein identification, candidate bands (i.e., those showing ≥2.0-fold change in fluorescence ratio of Cy3/Cy5 or Cy5/Cy3) were evaluated for detectability using a commercial, highly sensitive Coomassie blue staining kit (Simply Blue™ SafeStain; Invitrogen, Carlsbad, Calif.). Thus, only the five bands (A, B, C, D, and E; FIG. 4D) that could be detected by staining were excised for subsequent in-gel digestion and MS/MS analysis.

5. Nano-LC/ESI-MS/MS Analysis for Identification of DIGE Band Proteins

LC-MS/MS analysis was performed for protein identification of the Coomassie blue-stained bands with high Cy dye ratios. First, reduction with DTT and alkylation with indole-3 acetic add (IAA) was performed before treating each gel band with trypsin to digest the proteins in situ The samples were washed with 10 mM ammonium bicarbonate and 50% ACN, swollen in digestion buffer that contained 50 mM ammonium bicarbonate, 5 mM CaCl2, and 1 μg of trypsin, and then incubated at 37° C. for 16 h. Peptides were recovered by two cycles of extraction with 50 mM ammonium bicarbonate and 100% ACN. The resulting peptide extracts for each band were lyophilized and stored at −20° C. until MS analysis.

Lyophilized peptide samples were dissolved in mobile phase A for Nano-LC/ESI-MS/MS. MS/MS experiments for peptide identification were performed using a nano-LC/MS system that consisted of an Surveyor HPLC system (Thermo Electron Corporation, Waltham, Mass.) and an LTQFT mass spectrometer (ThermoFinnigan) equipped with a nano-ESI source. An autosampler was used to load 10 μl aliquots of the peptide solutions onto a C18 trap-column of i.d. 300 μm, length 5 mm, and particle size 5 μm (Dionex, Sunnyvale, Calif.). The peptides were desalted and concentrated on the column at a flow rate of 20 μl/min. The trapped peptides were then back-flushed and separated on a 100-mm home-made microcapillary column composed of C18 (Aqua; particle size 5 μm) packed into 75-μm silica tubing with an orifice i.d. of 6 μm.

Mobile phases A and B contained 0% and 80% acetonitrile, respectively. Each phase also contained 0.024% formic add and 0.5% acetic add. The gradient was started with 5% B for 15 min, ramped to 20% B over 3 min, to 60% over 47 min, to 95% over 2 min, held at 95% B for 5 min, and then ramped to 5% B for a further 2 min period. The column was equilibrated with 5% B for 6 min before the following run. The voltage applied to produce an electrospray was 2.1 kV. In each duty drde of mass analysis, one high-mass resolution (100,000) MS spectrum was acquired using the FT-ICR analyzer, followed by three data-dependent MS/MS scans using the linear ion trap analyzer. For MS/MS analysis, a normalized collision energy of 35% was used throughout the collision-induced dissociation (CID) phase.

The MS/MS spectra were analyzed using the following software and protocols. To identify the peptides, MASCOT version 2.1 (Matrix Science, London, UK), run on a local server, was used to search the IPI human protein database (v3.15.1 released by the European Bioinformatics Institute), which contains 57,846 protein sequences. MASCOT was used with monoisotopic mass selected with a precursor mass error of 1.5 Da, and fragment ion mass error of 0.8 Da. Trypsin was selected as the enzyme. Oxidized methionine, carbamidomethylated cysteine, propiomamide cysteine, and pyroglutamate (N-term E, Q) were chosen as variable modifications. Only those proteins identified by two or more high-scoring peptides were considered true matches. The high-scoring peptides corresponded to peptides that were above the threshold in our MASCOT search (expected <0.05, peptide score >42).

6. Determining the Most Abundant Protein in the Identified DIGE-Band

A single band on a gel usually contains several different proteins. However, the color of the fluorescence seems to be influenced by differences in one or more dominant proteins. To identify the dominant proteins in each band, we estimated the exponentially modified protein abundance index (emPAI) from the MASCOT search results. The emPAI provides an estimate of protein concentration from the number of peptide sequences of a protein identified by tandem mass spectrometry. The emPAI values represent an improvement over the protein abundance index (PAI), which is defined as the ratio between the number of peptides observed on tandem mass spectrometry and the number of peptides predicted from the amino acid sequence of the protein. PAI is based on the notion that peptides of more abundant proteins will appear more frequently in the database search results created using tandem mass spectrometry. PAI does not show a linear relationship to protein concentration, although it can be used to distinguish more-abundant proteins. The emPAI value, defined as ePAI-1, is approximately proportional to the protein concentration, and is useful for determining the absolute protein abundance. Through this process, we were able to identify the major proteins in each band based on the emPAI values. At each band, the most abundant protein showed much higher emPAI values than the second abundant protein. Among these major proteins, two dominant proteins were investigated further as potential biomarkers.

7. ELISA Based Quantification of Proteins in Serum Specimens from AML Patients and Healthy Controls High-emPAI proteins, which were considered to be differentially expressed between the two pooled samples by DIGE, can be important determinants for grouping the PreCR and CR sera of AML patients. We directly measured the levels of candidate proteins in the individual PreCR and CR samples by conventional ELISA using the corresponding antibodies. The proteins with the highest emPAI values among the component proteins identified in each of the five Coomassie blue-stained bands (A to E) with high Cy dye ratios were as follows: A, IGHM protein; B, 2-glycoprotein (or ApoH); C, hemopexin; D, CFH; and E, CFH. The protocol applied for proteins (CFH, Beta 2-glycoprotein) that were eventually confirmed to reflect Cy dye changes in the identified bands are described below.

The levels of CFH and ApoH in the serum were determined by using sandwich immunoassay method at room temperature. Briefly, the wells of 96-well microtiter plates were coated with 100 μl of mouse monoclonal antibody specific for human CFH (4.0 μg/ml in PBS; Abcam, Cambridge, UK) and for ApoH (mouse anti-ApoH monoclonal antibody, 2.0 μg/ml in PBS; Chemicon, Temecula, Calif.) and incubated overnight. After three washes with 100 μl of wash buffer (PBS), the wells were blocked with 300 μl of blocking buffer (4% skim milk in PBS) for 1 h. Each serum sample was diluted 1:2000 with blocking buffer, 100 μl of the diluted sample were added to each well, and the plates were incubated for 2 h. The wells were washed as described above with wash buffer and then incubated with 100 μl of goat polyclonal antibody specific for human CFH (2.0 μg/ml in blocking buffer; Abcam) and ApoH (rabbit anti-ApoH polyclonal antibody, 2.0 μg/ml in blocking buffer; Chemicon) for 2 h. The plates were washed again as described above, incubated with 100 μl of HRP-conjugated rabbit anti-goat antibody (2.5 μg/ml in blocking buffer; Southern Biotech, Birmingham, AL) and for ApoH, HRP-conjugated goat anti-rabbit antibody (2.5 μg/ml in blocking buffer; Southern Biotech) for 1 h, and washed three times.

For detection, 100 μl of substrate solution (1:1 $H_2O_2$:tetramethylbenzidine) was added to each well, the plates were incubated for 20 min, and then read at 450 nm on a VERSA max microplate reader (Molecular Devices, Sunnyvale, Calif.). Data analysis was performed using the SOFTMax Pro ver. 5 software (Molecular Devices). All of the data point were collected twice, and the detection values were shown as the means. Thereafter, ELISA-based quantifications for CFH and ApoH were performed for individual PreNR, NR, and Normal serum specimens.

8. Statistical Analysis

The statistical analysis was performed using SAS Software release 9.1, and the P-values reported are for two-tailed tests. After determining the CFH and ApoH levels in the individual PreCR, CR, PreNR, NR, and Normal samples by ELISA, we performed a normality test (Shapiro-Wilk test) and two-sample t tests to make comparisons between the following groups: PreCR vs. PreNR; CR vs. NR, and CR vs. Normal. Paired t-test was performed between the paired samples, PreCR vs. CR and PreNR vs. NR.

Results

1. MDLC and DIGE Analyses of Pooled PreCR and CR Serum Samples

Two pooled BM aspirate samples from AML patients in complete remission shown in Table 1 (CR group) were immunodepleted and labeled with Cy dyes, analyzed by CF and RP chromatography, and applied to one-dimensional polyacrylamide gel electrophoresis (1D-PAGE) as presented in FIG. 1.

TABLE 1

Clinical characteristics of patients with AML in the CR or NR group according to their responses to remission-induction chemotherapy

| Characteristics | CR group[a] | NR group[a] |
|---|---|---|
| Number of patients | 33 | 20 |
| Male/Female (%) | 14(42.4%)/19(57.6%) | 11(55.0%)/9(45.0%) |
| Age (mean ± S.D.), years | 43.97 ± 16.14 | 44.90 ± 15.17 |
| Diagnosis[b] | | |
| M0 | 1(3.0%) | 1(5.0%) |
| M1 | 0 | 1(5.0%) |
| M2 | 18(54.5%) | 9(45.0%) |
| M3 | 6(18.2%) | 3(15.0%) |
| M4 | 7(21.2%) | 2(10.0%) |
| M5 | 0 | 3(15.0%) |
| M6 | 1(3.0%) | 0 |
| M7 | 0 | 1(5.0%) |

[a]The CR group includes patients who achieved a morphologic leukemia-free state (<5% blasts in BM aspirate) and had neutrophil and platelet counts of >1,000/μl and >100,000/μl, respectively. Blasts with Auer rods or persistence of extramedullary disease should not be present. The NR group includes patients who did not achieve minimal blast counts or blood count recovery (i.e., ≥5% blasts in an aspirate sample or neutrophil or platelet counts of ≤1,000/μl or ≤100,000/μl, respectively).
[b]Diagnosis of AML according to the FAB classification: M0, undifferentiated; M1, AML without maturation; M2, AML with maturation; M3, promyelocytic leukemia; M4, acute myelomonocytic leukemia; M5, acute monocytic leukemia; M6, acute erythroleukemia; M7, acute megakaryocytic leukemia.

One of the two samples (designated as pooled CR), was produced by pooling 33 sera from AML patients who had achieved CR as a result of one month of remission-induction chemotherapy with idarubicin/BH-AC or ATRA. The other sample, designated as pooled PreCR, was produced by pooling from the same patients 33 sera that were obtained at the time of diagnosis, prior to chemotherapy.

Figure 2:
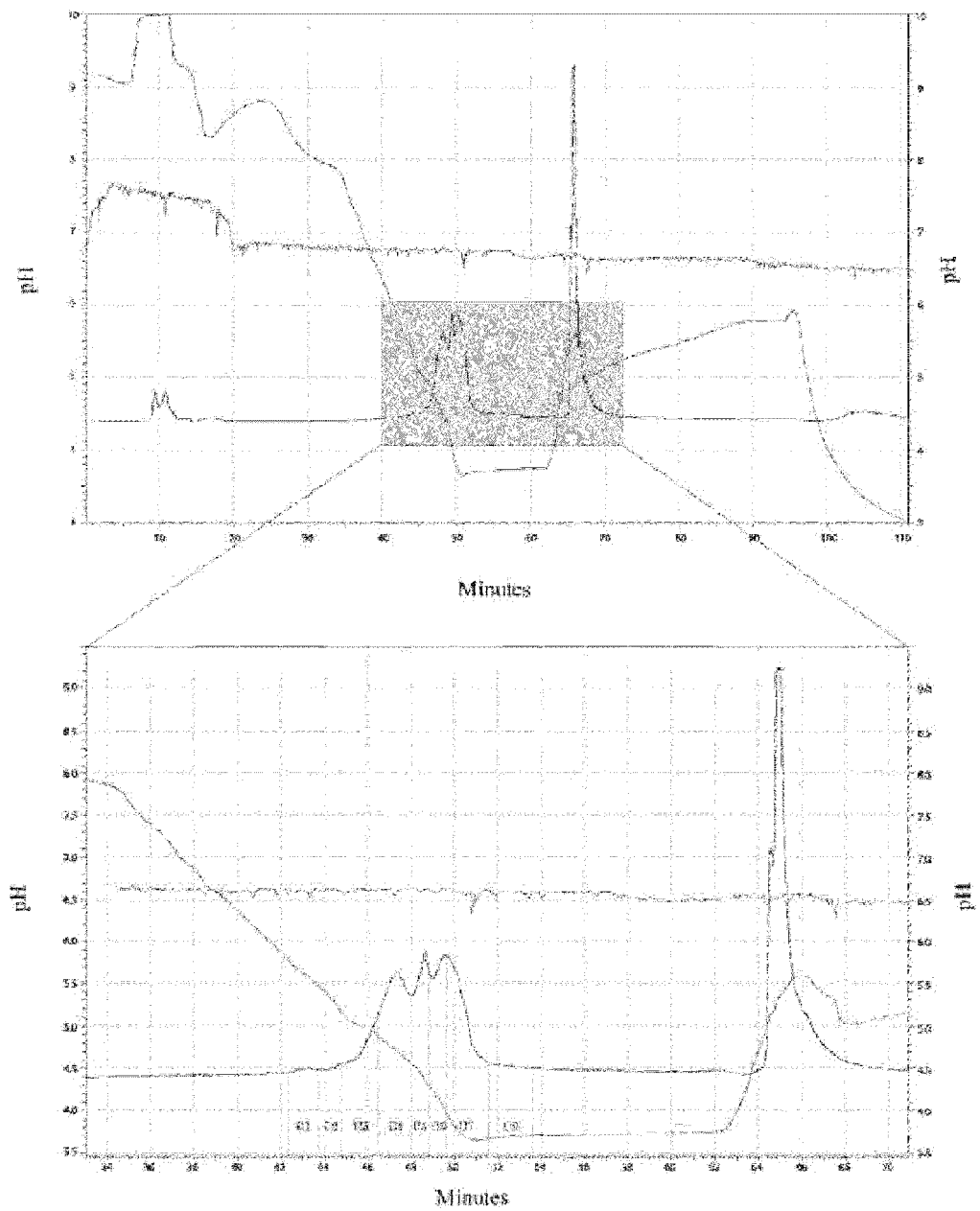
FIG. 2 shows CF chromatography results in the first dimension for separation of the mixture of Cy3-labeled (pooled PreCR) and Cy5-labeled (pooled CR) proteins. The two serum samples were immunodepleted prior to Cy dye labeling before CF chromatography. Separated fractions (C1 to C8) are shown.
Figure 3:
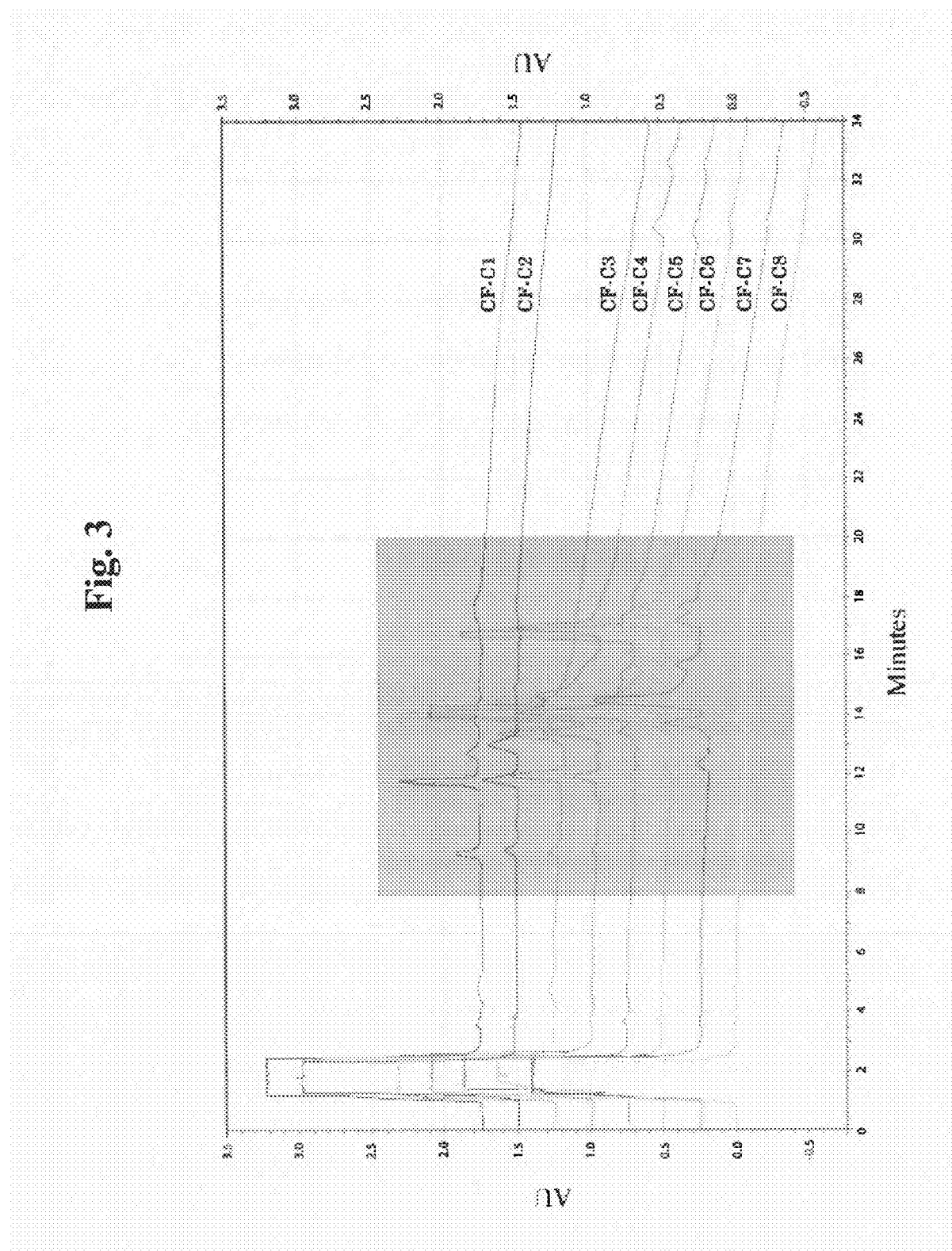
FIG. 3 shows RP chromatography results in the second dimension for separation of the chromatofocused samples (CF-C1 to CF-C8).

We obtained eight CF fractions (CF-C1 CF-C8) as illustrated in FIG. 2, and subsequent RP chromatography of each of the CF fractions produced 17 to 20 fractions, shown in FIG. 3. (CFC1: 17 frs, CFC2: 17 frs, CFC3: 17 frs, CFC4: 19 frs, CFC5: 19 frs, CFC6: 18 frs, CFC7: 20 frs, and CFC8: 17 frs)

Before separation on polyacrylamide gels, some of the fractions from RP chromatography were combined with the neighboring fractions to allow loading of equivalent amounts of protein. Without this step, the limited dynamic range of Cy3 and Cy5 fluorescence detection would not have been able to capture simultaneously both the high and low signals over the lanes of the gel. Forty three fractions of samples were prepared as above for the 1D-PAGE analysis.

Figure 4B:
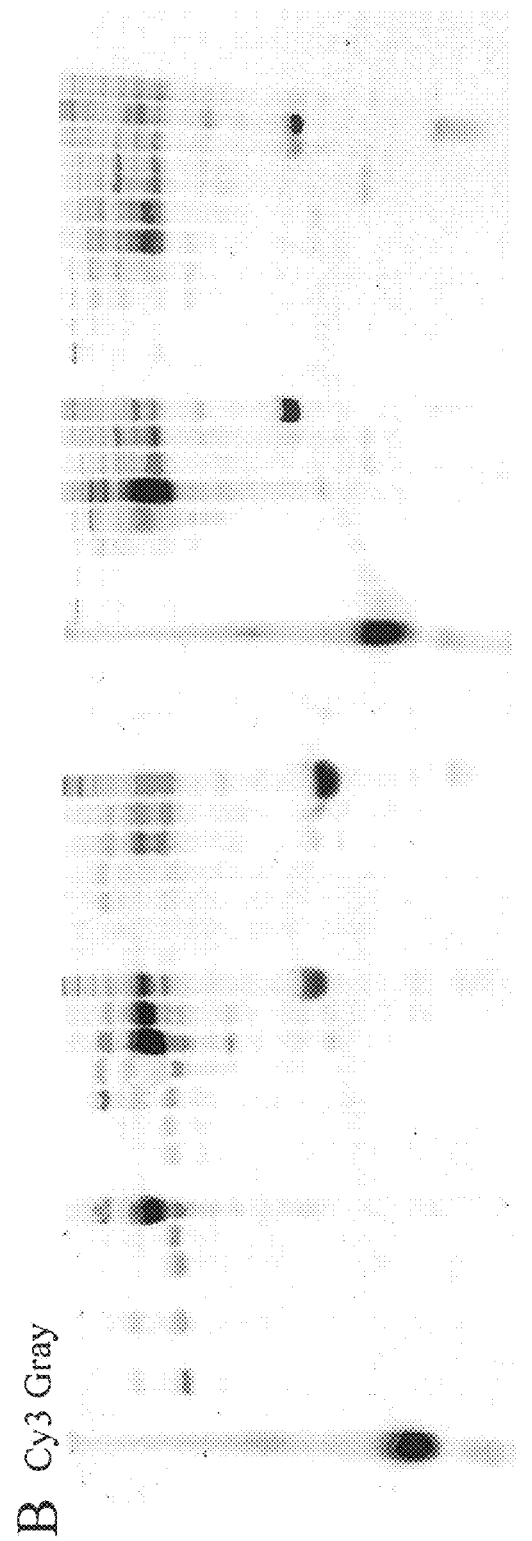
Figure 4D:
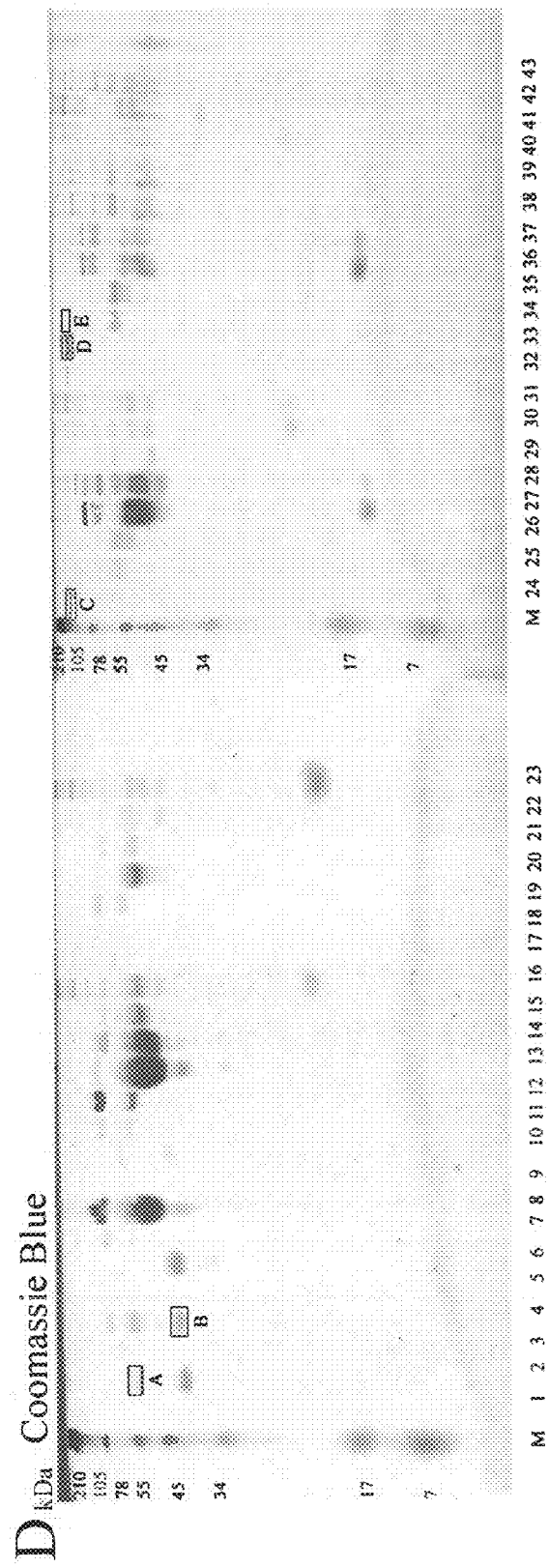

The results of the 1D-PAGE separation of these fractions, composed of Cy3- and Cy5-labeled protein mixtures, are shown in FIGS. 4A-4C. The protein bands in Cy3 and Cy5 images were analyzed with commercially available software, and the band intensity was calculated as intensity×area. Normalization of the raw Cy3 and Cy5 data revealed 10 bands that showed a ≥2.0-fold change in the Cy3/Cy5 volume ratio, whereas only three bands showed a ≥2.0-fold change in the Cy5/Cy3 volume ratio. Thirteen Cy dye positive bands were further stained with Coomassie blue. Five Coomassie blue stained bands were excised and subjected to in-gel digestion for MS/MS identification of the component proteins (A-E, FIG. 4D).

2. Identification of Band Proteins Showing Changes in Cy Dye-Labeled Protein Expression The five most abundant proteins of the component proteins in the excised gel bands identified by LTQ-FT MA/MS analysis and MASCOT searching are shown in Table 2.

TABLE 2 emPAI values for the five most abundant proteins in each of the gel bands A-E. These gel bands were excised, subjected to in-gel digestion, and analyzed by MS/MS for protein identification.

| Band | Accession Number | Protein Name | Protein Score | Observed | Observable | PAI | emPAI | Normalized Cy3/Cy5 |
|---|---|---|---|---|---|---|---|---|
| A | IPI00477090 | IGHM protein | 845.3 | 64 | 36 | 1.8 | 58.95 | 2.76 |
| | IPI00385264 | Ig mu heavy chain disease protein | 589.6 | 33 | 38 | 0.9 | 6.386 | |
| | IPI00022371 | Histidine-rich glycoprotein precursor | 712.4 | 33 | 55 | 0.6 | 2.981 | |
| | IPI00027462 | Protein S100-A9 | 208.8 | 9 | 15 | 0.6 | 2.981 | |
| | IPI00220327 | Keratin, type II cytoskeletal 1 | 1397.9 | 37 | 66 | 0.6 | 2.636 | |
| B | IPI00298828 | -2-Glycoprotein 1 precursor | 799.9 | 132 | 41 | 3.2 | 1657 | 2.71 |
| | IPI00295684 | Keratin 10 | 1483.7 | 39 | 48 | 0.8 | 5.494 | |
| | IPI00019359 | Keratin, type I cytoskeletal 9 | 1489.1 | 42 | 52 | 0.8 | 5.422 | |
| | IPI00220327 | Keratin, type II cytoskeletal 1 | 1755.6 | 47 | 66 | 0.7 | 4.154 | |
| | IPI00555784 | Keratin-associated protein 5-2 | 79.4 | 8 | 12 | 0.7 | 3.642 | |
| C | IPI00022488 | Hemopexin precursor | 715.9 | 92 | 46 | 2.0 | 99 | 2.04 |
| | IPI00029739 | Isoform 1 of CFH precursor | 3006.7 | 231 | 134 | 1.7 | 51.95 | |
| | IPI00555784 | Keratin-associated protein 5-2 | 108.5 | 10 | 12 | 0.8 | 5.813 | |
| | IPI00220327 | Keratin, type II cytoskeletal 1 | 1383.8 | 43 | 66 | 0.7 | 3.482 | |
| | IPI00295684 | Keratin 10 | 1014.7 | 24 | 48 | 0.5 | 2.162 | |
| D | IPI00515041 | CFH | 2593.2 | 223 | 44 | 5.1 | 1E+05 | 3.48 |
| | IPI00029739 | Isoform 1 of CFH precursor | 2959.7 | 253 | 134 | 1.9 | 76.28 | |
| | IPI00555784 | Keratin-associated protein 5-2 | 67.6 | 8 | 12 | 0.7 | 3.642 | |

TABLE 2-continued emPAI values for the five most abundant proteins in each of the gel bands A-E. These gel bands were excised, subjected to in-gel digestion, and analyzed by MS/MS for protein identification.

| Band | Accession Number | Protein Name | Protein Score | Observed | Observable | PAI | emPAI | Normalized Cy3/Cy5 |
|---|---|---|---|---|---|---|---|---|
|   | IPI00642651 | Metallothionein-1M | 49.1 | 4 | 7 | 0.6 | 2.728 |   |
|   | IPI00019359 | Keratin, type I cytoskeletal 9 | 1079.9 | 23 | 52 | 0.4 | 1.769 |   |
| E | IPI00515041 | CFH | 2051.9 | 98 | 44 | 2.2 | 167.8 | 2.34 |
|   | IPI00029739 | Isoform 1 of CFH precursor | 2323.0 | 111 | 134 | 0.8 | 5.735 |   |
|   | IPI00220327 | Keratin, type II cytoskeletal 1 | 1616.9 | 47 | 66 | 0.7 | 4.154 |   |
|   | IPI00019359 | Keratin, type I cytoskeletal 9 | 1309.5 | 32 | 52 | 0.6 | 3.125 |   |
|   | IPI00555784 | Keratin-associated protein 5-2 | 67.4 | 6 | 12 | 0.5 | 2.162 |   |

The protein abundance of the gel bands were determined from the emPAI of proteins identified through the MASCOT search. The relative abundance was also determined for the emPAI-selected proteins in each of the five gel bands. In each band, we identified major proteins with abundances>150% of those of the minor proteins. Across all the gel bands, there was only one major protein. Therefore, we selected the major proteins for each of the gel bands as follows: IGHM protein (A band), □β2-glycoprotein 1 (ApoH; B band), hemopexin (C band), and CFH (D and E bands). These proteins all showed ≥2.0-fold changes in the fluorescence ratio of Cy3/Cy5 (i.e., there were no proteins with ≥2.0-fold changes in Cy5/Cy3). Thereafter, the levels of the two proteins with the highest (or most convincing) emPAI values (i.e., apolipoprotein H, 1657; and CFH, 100,000) were evaluated to determine the statistical distributions of the PreCR (Cy3-labeled) and CR (Cy5-labeled) groups.

3. Confirmation of CFH and ApoH as Proteins that Distinguish Between the PreCR and CR Groups Evidence for the differential expression of CFH and ApoH in the leukemic serum specimens from individual PreCR and CR patients were obtained by ELISA. The samples for the ELISA included the same 33 paired sera used in the comparison of the two pooled samples, PreCR and CR, for MDLC-DIGE analysis. The CFH and ApoH levels in the individual PreCR and CR samples were determined by ELISA (Table 3) and compared by statistical analysis (Table 4).

TABLE 3

CFH and ApoH concentrations in the sera obtained from CR and NR AML patients before and after remission-induction chemotherapy, as well as from healthy controls (Normal).

| CFH (μg/ml) | CR (n = 33) | NR (n = 20) | Total (n = 53) | Normal (n = 25) |
|---|---|---|---|---|
| Before[1] |   |   |   |   |
| mean ± S.D.[3] | 627.91 ± 44.52 | 629.85 ± 34.64 | 628.64 ± 40.73 | 181.92 ± 51.02 |
| (median ± IQR)[3] | (630 ± 54) | (625.5 ± 42) | (627 ± 54) | (168 ± 66) |
| After[1] |   |   |   |   |
| mean ± S.D. | 176.82 ± 28.17 | 617.7 ± 43.19 | 343.19 ± 218.45 |   |
| (median ± IQR) | (177 ± 39) | (610.5 ± 66) | (201 ± 430.5) |   |
| ApoH (μg/ml) | CR (n = 33) | NR (n = 20) | Total (n = 53) | Normal (n = 25) |
| Before[2] |   |   |   |   |
| mean ± S.D.[3] | 610 ± 38.66 | 619.95 ± 40.64 | 613.75 ± 39.33 | 191.92 ± 44.54 |
| (median ± IQR)[3] | (612 ± 39) | (618 ± 60) | (615 ± 43.5) | (183 ± 72) |
| After[2] |   |   |   |   |
| mean ± S.D. | 181.55 ± 39.81 | 606.6 ± 48.79 | 341.94 ± 212.39 |   |
| (median ± IQR) | (189 ± 60) | (600 ± 73.5) | (213 ± 405) |   |

[1]CFH and
[2]ApoH concentrations before and after remission-induction chemotherapy.
[3]S.D., standard deviation;
IQR, interquartile range.

TABLE 4

Comparison of the CFH and ApoH values for PreCR vs. PreNR, PreCR vs. CR, PreNR vs. NR, CR vs. NR, and CR vs. Normal.

| Group | Protein | | Concentration (mean ± S.D) | t | P-value |
|---|---|---|---|---|---|
| PreCR vs. | CFH | $\Delta CFH_{CR} = CFH_{preCR} - CFH_{CR}$ | 451.09 ± 47.89 | 54.11 | 0.001 |

TABLE 4-continued

Comparison of the CFH and ApoH values for PreCR vs. PreNR,
PreCR vs. CR, PreNR vs. NR, CR vs. NR, and CR vs. Normal.

| Group | Protein | | Concentration (mean ± S.D) | t | P-value |
|---|---|---|---|---|---|
| CR | ApoH | $\Delta ApoH_{CR} = ApoH_{preCR} - ApoH_{CR}$ | 428.45 ± 50.05 | 49.18 | 0.000 |
| PreNR vs. NR | CFH | $\Delta CFH_{NR} = CFH_{preNR} - CFH_{NR}$ | 12.15 ± 61.81 | 0.88 | 0.3903 |
| | ApoH | $\Delta ApoH_{NR} = ApoH_{preNR} - ApoH_{NR}$ | 13.35 ± 70.68 | 0.84 | 0.4088 |
| PreNR vs. PreCR | CFH | $CFH_{preNR}$ $CFH_{preCR}$ | 629.85 ± 34.64 627.91 ± 44.52 | −0.17 | 0.8684 |
| | ApoH | $ApoH_{preNR}$ $ApoH_{preCR}$ | 619.95 ± 40.64 610.0 ± 38.66 | 0.89 | 0.3772 |
| NR vs. CR | CFH | $CFH_{NR}$ $CFH_{CR}$ | 617.7 ± 43.19 176.82 ± 28.17 | −40.70 | 0.001 |
| | ApoH | $ApoH_{NR}$ $ApoH_{CR}$ | 606.6 ± 48.79 181.55 ± 39.81 | −34.58 | 0.001 |
| CR vs. Normal | CFH | $CFH_{CR}$ $CFH_{Normal}$ | 176.82 ± 28.17 181.92 ± 51.02 | −0.45 | 0.6550 |
| | ApoH | $ApoH_{CR}$ $ApoH_{Normal}$ | 181.55 ± 39.82 191.28 ± 44.54 | −0.88 | 0.3847 |

Figure 5:
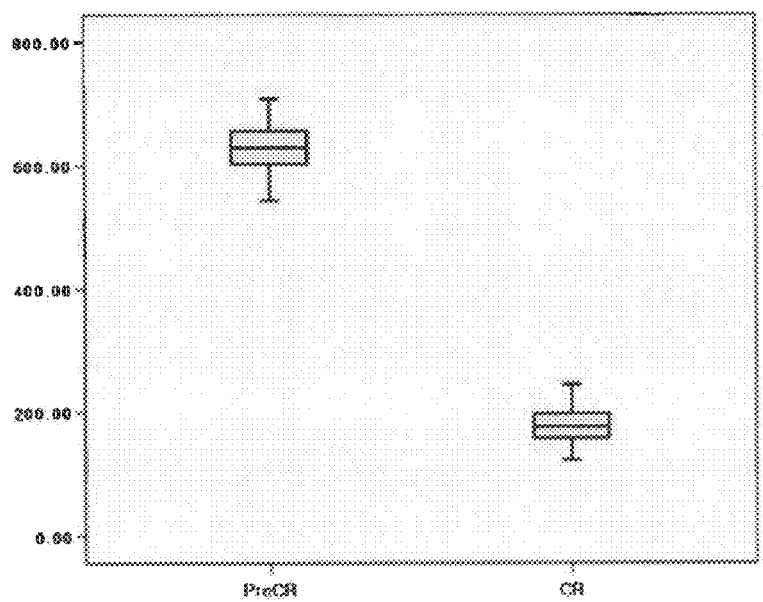
FIG. 5 shows box plots of the CFH and ApoH protein levels (μg/ml) in the sera from patients with AML PreCR indicates pre-treatment samples (at the time of AML diagnosis) obtained from patients who had achieved complete remission (CR). The pooled PreCR and CR samples were used for MDLC-DIGE protein profile analysis, as shown in FIG. 4.
Figure 5:
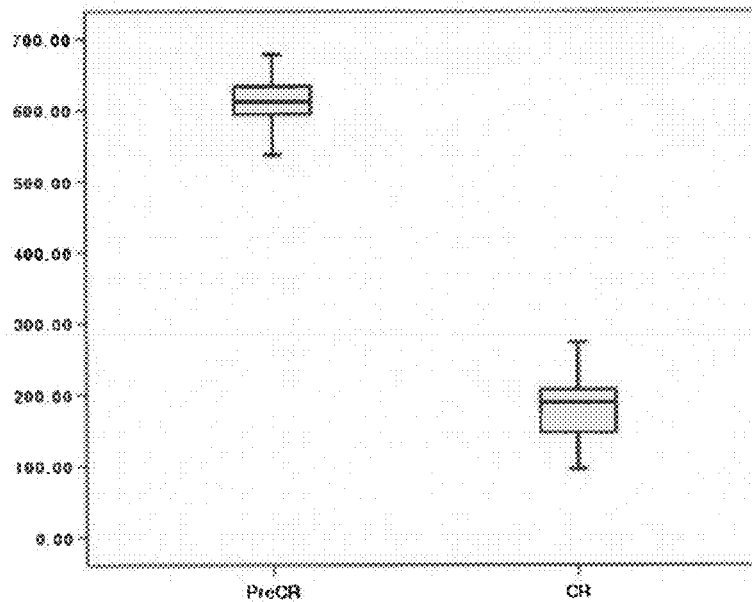

Box-and-whisker plots graphically depicting the results of these comparisons are shown in FIG. 5. The Shapiro-Wilk test revealed a normal distribution (P>0.05) of delta values in CR patients for CFH levels (i.e., $deltaCFH_{CR} = CFH_{preCR} - CFH_{CR}$) and for ApoH levels (i.e., $deltaApoH_{CR} = ApoH_{preCR} - ApoH_{CR}$). The parametric paired t-test was used to test the null hypothesis that there were no mean differences between the paired observations for $CFH_{CR}$ and $CFH_{preCR}$ or $ApoH_{CR}$ and $ApoH_{preCR}$. The mean (±S.D.) delta values of CFH and ApoH in CR patients were 451.09±47.89 and 428.45±50.05, with P-values of 0.001 and 0.000, respectively. Therefore, the null hypothesis that there were no mean difference between the paired observation for $CFH_{CR}$ and $CFH_{preCR}$ or $ApoH_{CR}$ and $ApoH_{preCR}$ were rejected. Thus, the differences between PreCR and CR CFH levels and between PreCR and CR ApoH levels were statistically significant.

4. ELISA-Based Quantification of CFH and ApoH in the Sera of AML Patients

Figure 6:
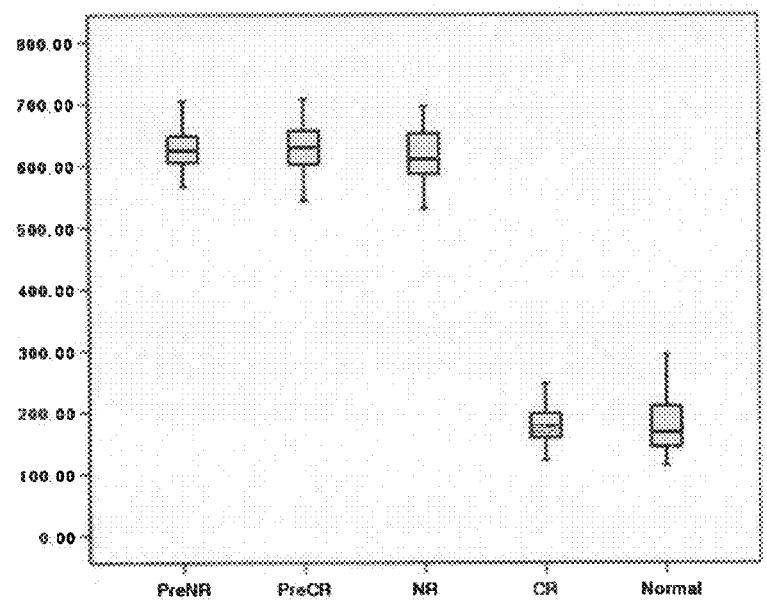
FIG. 6 shows box plots of the CFH and ApoH protein levels (μg/ml) in sera from AML patients in various disease states. PreNR indicates samples pre-treatment samples (at the time of AML diagnosis) obtained from patients who failed to achieve complete remission (non-remission, NR). Normal indicates samples from healthy volunteers, used as controls.
Figure 6:
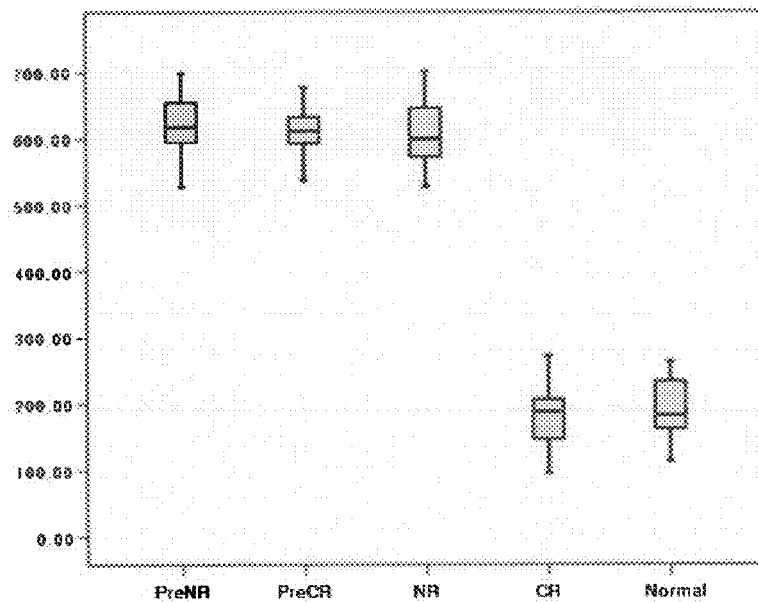

The quantification of CFH and ApoH levels by ELISA (Table 3) and the results of statistical analysis (Table 4) were conducted for the other serum specimens from AML patients, such as PreNR and NR, as well as for the specimens from healthy controls (Normal). Box-and-whisker plots graphically depicting the results of these comparisons are shown in FIG. 6.

The Shapiro-Wilk test revealed a normal distribution (P>0.05) of delta values in NR patients for CFH levels (i.e., $deltaCFHNR = CFH_{preNR} - CFH_{NR}$) and for ApoH levels (i.e., $deltaApoH_{NR} = ApoH_{preNR} - ApoH_{NR}$). The paired t-test was used to test the null hypotheses that there were no mean differences between the paired observations for $CFH_{NR}$ and $CFH_{preNR}$ or $ApoH_{NR}$ and $ApoH_{preNR}$. The mean delta values of CFH and ApoH in NR patients were 12.15±61.81 and 13.35±70.68, with P-values of 0.3903 and 0.4088, respectively. Thus, the null hypotheses that there were no mean differences between $CFH_{preNR}$ and $CFH_{NR}$ or between $ApoH_{preNR}$ and $ApoH_{NR}$ could not be rejected. The differences between the PreNR and NR CFH levels and between the PreNR and NR ApoH levels were not statistically significant.

Likewise, the Shapiro-Wilk test revealed a normal distribution (P>0.05) of PreNR, PreCR, NR, CR, and Normal for the CFH levels (i.e., $CFH_{PreNR}$, $CFH_{PreCR}$, $CFH_{NR}$, $CFH_{CR}$, and $CFH_{Normal}$) and for the ApoH levels (i.e., $ApoH_{PreNR}$, $ApoH_{PreCR}$, $ApoH_{NR}$, $ApoH_{CR}$, and $ApoH_{Normal}$). The two-sample t-test was used to test the null hypotheses that there were no mean differences between $CFH_{PreNR}$ and $CFH_{PreCR}$, $CFH_{NR}$ and $CFH_{CR}$, and $CFH_{CR}$ and $CFH_{Normal}$; and then between $ApoH_{PreNR}$ and $ApoH_{PreCR}$, $ApoH_{NR}$ and $ApoH_{CR}$, and $ApoH_{CR}$ and $ApoH_{Normal}$.

The mean CFH values for PreNR and PreCR, NR and CR, and CR and Normal were: 629.85±34.64 and 627.91±44.52 (P=0.8684); 617.7±43.19 and 176.82±28.17 (P=0.001), and 176.82±28.17; and 181.92±51.02 (P=0.6550), respectively. Thus, the difference in CFH level between NR and CR, but not between CR and Normal or between PreNR and PreCR was statistically significant.

In addition, the mean ApoH values for PreNR and PreCR, NR and CR, and CR and Normal were: 619.95±40.64 and 610.0±38.66 (P=0.3772); 606.6±48.79 and 181.55±39.81 (P=0.001); and 181.55±39.82 and 191.28±44.54 (P=0.3847), respectively. Thus, the difference in ApoH level between NR and CR, but not between PreNR and PreCR or between CR and Normal, was statistically significant.

As described previously, the inventor used multidimensional liquid chromatography (MDLC) and differential gel electrophoresis (DIGE) to perform qualitative and quantitative analyses of the protein profiles of pooled CR and PreCR serum samples from AML patients. This technology may be categorized as a protein-labeling method for direct profiling of proteins, in contrast to peptide-labeling methods, such as iTRAQ an ICAT, which are used to conduct indirect profiling of proteins. Wang et al. have reported that an orthogonal three-dimensional intact-protein analysis system (IPAS), comprising sequential separation of immunodepleted and Cy dye-labeled proteins using isoelectric focusing, RP chromatography and one-dimensional SDS-PAGE, provided both comprehensive profiling and quantitative analysis in disease-related applications.

In this invention, the present inventor modified the three-dimensional IPAS to search for the marker proteins, capable of distinguishing two different groups of AML patient sera. First, the neighboring fractions of the proteins separated from the second dimension (i.e., RP chromatography) were pooled, so that the total amount of protein in each lane on separation in the third dimension (i.e., SDS-PAGE) was similar. Without this adjustment, the amounts of proteins in the lanes would vary too much to be within the limits of the dynamic intensity range of the scanner (9200 Typhoon™; GE Healthcare). Second, to identify the most abundant proteins affecting the Cy3/Cy5 ratios of the protein bands on DIGE, the emPAI was computed for all the MS-identified proteins in the excised bands. Third, the two top emPAI-ranked proteins, CFH and ApoH, among the five candidates with the highest emPAI scores in the respective bands were evaluated by ELISA for their individual levels in the PreCR and CR groups of serum samples. The results indicate that these two proteins had are classifiers capable of distinguishing between PreCR and CR groups in AML patients.

Thereafter, the inventor expanded the ELISA-based quantification of CFH and ApoH to other serum samples from AML patients and healthy subjects. The levels of CFH and ApoH in the PreNR and NR samples of the patients were measured and compared with those in the PreCR and CR samples and those in the healthy controls (Normal). The results indicate that the serum concentrations of CFH and ApoH differ between AML patients and healthy subjects. In terms of the statistical distribution of serum CFH and ApoH, AML patients and healthy controls can be divided into two groups: high CFH/ApoH levels and low CFH/ApoH levels.

Thus, the sera of patients in the leukemic cell-loaded state (PreCR, PreNR, and NR) showed high levels of CFH and ApoH, while the sera of patients in the leukemic cell-unloaded state (CR and Normal) showed low levels of CFH and ApoH.

The patients with AML who did not achieve CR, designated as non-remission (NR), were categorized into two groups. First, in accordance with the revised recommendations of the IWG (2003) for the standardization of response criteria, patients in the morphologic leukemia-free state (i.e., <5% blasts in the BM aspirate) but not in the blood count recovery state (i.e., neutrophil or platelet counts of ≤1,000/μl or ≤100,000/μl, respectively) were defined as morphologic CR with incomplete blood count recovery (CRi). CRi is treated as a special category, consisting of patients who fulfill the morphologic criteria for CR. Second, according to the same IWG criteria, patients who are not in the morphologic leukemia-free state but in the blood count recovery state, and those who are in neither the morphologic leukemia-free state nor the blood count recovery state are defined as treatment failures due to resistant disease or relapse.

Based on the results of the present invention, patients with AML in the morphologic leukemia-free state but without blood count recovery would not meet the response criteria of CR. The standard of the morphologic leukemia-free state should not be the sole consideration in deciding whether an AML patient has achieved CR. Judging from the patterns of the CFH and ApoH levels in sera, the CRi state of an AML patient may not be different from that of a patient in treatment failure. This notion is supported by the previous report of Georgine et al., who showed that platelet and neutrophil counts are independent prognostic factors determining OS and RR. Therefore, AML patients in the CRi state should not be regarded as being in CR in terms of recovery from disease status.

The results of the statistical analyses indicate that serum CFH and ApoH are good classifiers or biomarkers for distinguishing between the states of CR and NR. Platelets and neutrophils frequently show changes in morphology after chemotherapy, such that even a blood cell counter does not reflect an authentic measurement of blood cell counts. The counting of BM blasts without an aspirate sample that contains BM spicules and ≥200 nucleated cells, as in diluted specimens due to inadequate sampling of BM, does not provide an accurate assessment of blast percentages in the BM samples from AML patients. In such cases, measurements of serum CFH and ApoH may represent a valuable alternative for assessing the remission status of a patient. In addition, the serum CFH and ApoH levels can be determined simply using a conventional ELISA.

Complement factor H, which is a 150-kDa single-chain plasma glycoprotein, plays a pivotal role in the regulation of alternative pathway complement activation and possesses anti-inflammatory activities. Complement factor H acts as a cofactor for factor I in the degradation of newly formed C3b molecules, and also shows decay accelerating activity in controlling the formation and stability of the C3 convertase C3bBb. The secreted plasma protein is organized into 20 homologous units, termed shot consensus repeats (SCRs). Structure-function analyses have located three distinct binding regions on CFH for its most important ligand, C3b.

Complement factor H is implicated in recurrent infections by microorganisms, such as *Streptococcus pyogenes, Borrelia burgdorferi, Neisseria gonorrheae, Neisseria meningitidis, Yersinia enterocolitica, Echinococcus granulosus,* and HIV. Pathogens mimic the surface structures of host cells to acquire CFH for the control of complement activation (i.e., for evading immune surveillance).

The BTAstat and BTA TRAK tests are new immunoassays that detect and measure target antigens in the urine of individuals diagnosed with urinary bladder cancer. Kinders et al. have reported that the antigens recognized by the two monoclonal antibodies in the BTA tests are derived from CFH. They also demonstrated by RT-PCR and the BTA TRAK assay that several human bladder, cervical, and renal cancer cell lines, but not normal human epithelial keratinocytes, a myeloid leukemia cell line (HL-60) or a colon cancer cell line, produce and secrete CFH. Thus, it has been suggested that the synthesis of CFH by some cancer cells is an effective method of evading host immune surveillance.

ApoH (or β2 glycoprotein I; β2GPI) is a 54-kDa single-chain protein of 326 amino acids and contains four N-linked glycosylation sites. ApoH consists of five repeat sequences, known as short consensus repeats (SCRs). The fifth domain contains a conserved, positively charged region between cysteines 281 and 288 that is critical for the binding of negatively charged phospholipids. Although the exact physiologic function of ApoH is unknown, it is believed to exert an anticoagulant effect by displacing various coagulant proteins from the anionic phospholipid sites. Recently, ApoH has been shown to bind to factor (F) XI in vitro at concentrations lower than those of the protein in human plasma, and this binding inhibits FXI activation to FXIa by thrombin and FXIIa. Proteolytic cleavage of the fifth domain of ApoH abolishes its inhibitory effect on FXI activation, while retaining its ability to bind FXIa, and results in a reduced ability of the cleaved ApoH to bind phospholipids. Trousseau's syndrome is defined as recurrent episodes of venous thrombosis, thrombophlebitis or arterial thrombi due to non-bacterial endocarditis in patients with underlying malignancies. The prevalence of clinically apparent venous thromboembolism in cancer patients may be up to 15%. Several factors have been implicated in malignancy-relevant thrombosis, including the release of tissue factors, cancer-related procoagulants, tumor cell-secreted mucin, changes in viscosity, and tumor seeding. Thrombotic complications in patients with malignancy occur at a high frequency, and other factors, such as surgery and chemotherapy, potentiate this risk.

These observations raise the question as to why the levels of the complement deactivator CFH and the anticoagulant ApoH are much higher in AML patients with overt illness at diagnosis and NR after chemotherapy than for subjects in the healthy state or in CR after chemotherapy. Two different explanations can be given, depending on whether the indicator proteins, CFH and ApoH, are being produced by malignant or normal cells.

If CFH and ApoH are leakage proteins from the leukemic cells of AML patients, the cancer cells would express these proteins to evade the immune surveillance (CFH) and coagulation activity (ApoH) of the host. Stirewalt et al. reported the results of a microarray (Affymetrix HG-U133A) analysis of gene expression levels in AML, involving on a study population of 311 leukemic patients and 38 normal controls. Their data indicate that the levels of CFH and ApoH gene expression in AML patients are neither decreased nor increased in comparison to those in normal controls (http://www.ncbi.nlm.nih.gov/geo/query/acc.cgi).

However, if CFH and ApoH are reactant proteins from the normal cells of patients with AML, the normal cells, such as hepatocytes, would express these proteins to protect the host from malignancy through the down-regulation of dysfunctional complement and coagulation systems. Interestingly, in the present study, all of the patients who showed morphologic CR with incomplete blood count recovery (CRi) had high levels of CFH and ApoH. That is, there were no statistically significant differences between the CFH and ApoH concentrations of the CRi and the other NR specimens, with P<0.01. It appears that the serum levels of CFH and ApoH remain high until the normal blood cells show recovery to the normal range.

These observations, taken together with the data reported by Stirewalt et al. regarding gene expression in AML patients, suggest that factors related to the tumor alone do not determine the high or normal levels of the two indicators; instead, host factors expressed in response to the tumor may determine the CFH and ApoH levels in AML patients who are in CR or NR.

In conclusion, using MDLC-DIGE profiling technology and ELISA-based protein quantification, we have demonstrated that the serum CFH and ApoH levels in AML patients in CR are normal, whereas the levels of these two proteins are elevated in patients who have failed to achieve CR (non-remission, NR). Complement factor H and ApoH are shown to be valuable markers for distinguishing between CR and NR.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

1 Kasper D L, Braunwald E, Fauci A S, Hauser S L, Longo D L, Jameson J L. Harrison's Principles of Internal Medicine. NY: McGraw-Hill, 2004: 631-41.
2 de Greef G E, van Putten W L J, Boogaerts M, et al. Criteria for defining a complete remission in acute myeloid leukaemia revisited. An analysis of patients treated in HOVON-SAKK co-operative group studies. Brit J Haematol 2004; 128: 184-91.
3 Cheson B D, Bennett J M, Kopecky K J, et al. Revised recommendations of the International Working Group for Diagnosis, Standardization of Response Criteria, Treatment Outcomes, and Reporting Standards for Therapeutic Trials in Acute Myeloid Leukemia. J Clin Oncol 2003; 21: 4642-49.
4 Wu S L, Amato H, Biringer R, Choudhary G, Shieh P, Hancock W S. Targeted proteomics of low-level proteins in human plasma by LC/MSn: using human growth hormone as a model system. J Proteome Res 2002; 1: 459-65.
5 Ishihama Y, Oda Y, Tabata T, Sato T, Nagasu T, Rappsilber J. Exponentially modified protein abundance index (emPAI) for estimation of absolute protein amount in proteomics by the number of sequenced peptides per protein. Mol Cell Proteomics 2005; 4: 1265-72.
6 Rappsilber 3, Ryder U, Lamond A I, Mann M. Large-scale proteomic analysis of the human spliceosome. Genome Res 2002; 12: 1231-45.
7 Wang H, Clouthier, S G, Galchev V, Misek D E, Duffner U, Min C K. Intact-protein-based high-resolution three-dimensional quantitative analysis system for proteome profiling of biological fluids. Mol Cell Proteomics 2005; 4: 618-25.
8 Zipfel P F. Hemolytic uremic syndrome: how do factor H mutants mediate endothelial damage? Trends Immunol 2001; 7: 345-8.
9 Zipfel P F, Hellwage J, Friese M A, Hegasy G, Jokiranta S T, Meri S. Factor H and disease: a complement regulator affects vital body functions. Mol Immunol 1999; 36: 241-8.
10 Lindahl G, Sjöbring U, Johnsson E. Human complement regulator: a major target for pathogenic microorganism. Curr Opin Immunol 2000; 12: 44-51.
11 Kinders R, Jones T, Root R, et al. Complement factor H or a related protein is a marker for transitional cell cancer of the bladder. Clin Cancer Res 1998; 4: 2511-20.
12 Miyakis S, Giannakopoulos B, Krilis S A. Beta 2 glycoprotein I—function in health and disease. Thromb Res 2004; 114: 335-46.
13 Sheng Y, Sali A, Herzog H, Lahnstein J, Krilis S A. Site-directed mutagenesis of recombinant human beta 2-glycoprotein I identifies a cluster of lysine residues that are critical for phospholipid binding and anti-cardiolipin antibody activity. J Immunol 1996; 157: 3744-51.
14 Reddel S W, Krilis S A. The anti-phospholipid syndrome. In: Theofilopoulos A N, Bone C A, editors. The Molecular Pathology of Autoimmune Diseases. NY: Taylor and Francis, 2002: 325-52.
15 Shi T, Iverson G M, Qi J C, et al. Beta 2-Glycoprotein I binds factor XI and inhibits its activation by thrombin and factor XIIa: loss of inhibition by clipped beta 2-glycoprotein I. Proc Natl Acad Sci USA 2004; 101: 3939-44.
16 Rickles F R, Edwards R L. Activation of blood coagulation in cancer: Trousseau's syndrome revisited. Blood 1983; 62: 14-31.
17 Rickles F R, Levine M, Edwards R L. Hemostatic alterations in cancer patients. Cancer Metastasis Rev 1992; 11: 237-48.
18 Ideguchi H, Ohno S, Ueda A, Ishigatsubo Y. Catastrophic antiphospholipid syndrome associated with malignancies (case report and review of the literature). Lupus 2007; 16: 59-64.
19 Stirewalt D L, Meshinchi S, Kopecky K J, et al. Identification of genes with abnormal expression changes in acute myeloid leukemia. Gene Chromosome Canc 2007; 47: 8-20.

What is claimed is:

1. A method for determining complete remission or non-remission in a patient with acute myeloid leukemia (AML) after chemotherapy, which comprises measuring the level of CFH (complement factor H) or ApoH (apolipoprotein H) in a biological sample selected from the group consisting of blood, serum and plasma from the AML patient by immunoassay, wherein a level of 500-700 µg/ml of CFH or ApoH indicates that the patient is in a non-remission in AML, wherein a similar level of CFH or ApoH compared to the levels thereof in blood, serum or plasma from a normal human indicates that the patient achieves complete remission in AML, and wherein the similar level of CFH or ApoH to the normal human is between +50 µg/ml and −50 µg/ml of a level of CFH or ApoH in the normal human.

2. The method according to claim 1, wherein the biological sample is serum.

3. The method according to claim 1, wherein the patient with AML is determined to achieve complete remission in AML when the level of CFH or ApoH is measured to be 130-250 µg/ml.

4. The method according to claim 3, wherein the patient with AML is determined to achieve complete remission in AML when the level of CFH is measured to be 176.82 ±28.17 µg/ml.

5. The method according to claim 3, wherein the patient with AML is determined to achieve complete remission in AML when the level of ApoH is measured to be 181.55 ±39.81 μg/ml.

6. The method according to claim 1, wherein the patient with AML is determined to be in non-remission in AML when the level of CFH is measured to be 617.7 ±43.19 μg/ml.

7. The method according to claim 1, wherein the patient with AML is determined to be in non-remission in AML when the level of ApoH is measured to be 606.6 ±48.79 μg/ml.

* * * * *